United States Patent [19]

Bathe et al.

[11] Patent Number: 5,678,537
[45] Date of Patent: Oct. 21, 1997

[54] OXYGEN FLUSH FOR ANESTHESIA SYSTEMS

[75] Inventors: Duncan P. L. Bathe; John R. Pinkert; Robert Q. Tham; Wilfried R. Peickert, all of Madison, Wis.

[73] Assignee: Ohmeda Inc., Liberty Corner, N.J.

[21] Appl. No.: 620,064

[22] Filed: Mar. 21, 1996

[51] Int. Cl.$^6$ .................................................. A61M 15/00
[52] U.S. Cl. .......................... 128/203.12; 128/203.14; 128/203.25
[58] Field of Search .................... 128/203.12, 203.14, 128/203.19, 203.25, 202.22

[56] References Cited

U.S. PATENT DOCUMENTS

| | | | |
|---|---|---|---|
| 4,034,753 | 7/1977 | Connel | 128/203.12 |
| 4,148,312 | 4/1979 | Bird | 128/203.28 |
| 4,345,612 | 8/1982 | Koni et al. | 128/203.25 |
| 4,434,790 | 3/1984 | Olesen | 128/203.12 |
| 4,442,856 | 4/1984 | Betz | 128/202.22 |
| 4,991,576 | 2/1991 | Henkin et al. | 128/911 |

*Primary Examiner*—Aaron J. Lewis
*Attorney, Agent, or Firm*—Roger M. Rathbun; R. Hain Swope

[57] ABSTRACT

A system is disclosed to prevent the build up of pressure within a patient circuit when an oxygen flush is activated in a ventilator powered anesthesia system. In the event the user activates the oxygen flush at a time that the ventilator is in the inhalation cycle providing a breath to the patient, a valve is automatically opened to vent the patient circuit to the atmosphere, thereby preventing that additional oxygen flow to the patient circuit from resulting in an undesirable pressure build up that could affect the lungs of the patient.

16 Claims, 2 Drawing Sheets

OXYGEN FLUSH FOR ANESTHESIA SYSTEMS

BACKGROUND OF THE INVENTION

The present invention relates to anesthesia systems used to provide an anesthetic agent to a patient undergoing an operation.

In general, anesthesia systems are utilized in operating rooms and comprise various equipment necessary to anesthetize the patient and maintain the patient in that state until the operation is completed and it is possible to terminate the introduction of the anesthetic agent.

Such systems comprise various pressure regulators, flow control devices, gas mixing devices and vaporizers to vaporize a volatile liquid anesthetic and to introduce the anesthetic laden gases into the patient. The patient is connected to the system by means of a face mask or other device and which interfaces with the anesthesia system via a patient circuit that may typically have an inspiratory limb through which the gases are introduced into the patient and an expiratory limb that conveys the exhaled gases from the patient. Such limbs may be separate conduits joined by a wye piece at or near the patient or may comprise coaxial conduits commonly known as Bain circuits.

In a typical anesthesia system, the overall flow of gases to and from the patient may be in a generally closed circuit, that is, the patient is connected to a substantially closed loop supply of gasses and rebreathes certain of those exhaled gases supplemented by fresh gas. Alternatively, the patient circuit could be an open circuit and all of the exhaled gases simply vented or channeled from the system to an external environment and not rebreathed by the patient. Other variety of circuits are used that deliver the anesthetic gases to the patient, such as semi-open circuits and the like.

As the driving force to the patient, a ventilator is used and which basically breathes for the patient since the patient is under anesthesia and is unable to carry out the normal spontaneous breathing functions. The ventilator, therefore, provides a quantity of the gas containing a predetermined metered quantity of the anesthetic agent along with other gases such as $N_2O$ and, of course, a life sustaining percentage of oxygen.

That gas containing the anesthetic may be delivered directly by the ventilator into the patient circuit for introduction to the patient or may include an intermediate mechanism such as a bellows. In the latter case, the gas from the ventilator does not contain the anesthetic agent but is used to simply power the bellows to collapse that bellows to deliver the aforementioned anesthetic containing gas from the bellows to the patient.

With the use of a bellows, the patient is basically isolated from the ventilator and it is possible to use the bellows to allow rebreathing of the patients exhaled gases to conserve those gases including the anesthetic agent.

Such ventilators have two cycles, an inhalation cycle where gas is being forced into the patient and an exhalation cycle where the ventilator allows the patient to exhale through an exhalation valve that vents some of the exhaled gases from the system. The ventilator, therefore, controls both the patient's inhalation and exhalation and the overall circuit is fairly restricted with respect to gases from the overall system being vented to the surrounding ambient.

One component of the anesthesia system is an exhalation valve that opens to allow the patient to exhale. That exhalation valve is normally controlled by the anesthesia system in synchronism with the breathing cycles of the ventilator, that is, when the ventilator is in its inhalation mode providing a breath to the patient, the exhalation valve is closed. On the other hand, when the ventilator is in its exhalation mode, the exhalation valve is to relieve the pressure of within the bellows container so that the patient can exhale and raise the gas reservoir, or bellows to its inflated state.

Control of the exhalation valve is normally carried out by the CPU operating the ventilator, or may simply be by some pneumatic or electrical function in the anesthesia system. In any case, there is, of course, a need to synchronize the operation of the exhalation valve with the particular cycle of the ventilator.

Another typical function of such anesthesia systems is the oxygen flush that is manually operated by the user to provide an instant flush of $O_2$ into the patient breathing circuit. The $O_2$ flush is commonly used to recharge the bellows in the case of a leak in the patient circuit or to rapidly purge the patient circuit of anesthetic gases in the event of an overdose of the anesthetic agent. The latter function is carried out whether or not there is a bellows being used in the anesthesia system and may be used where the anesthetic gases are supplied directly to the patient circuit from the ventilator.

Generally, a manual valve is pushed by the user to activate the $O_2$ flush and the button, when released, stops the flush. When activated, the excess oxygen from the flush stream of $O_2$ is released by means of a popoff valve in the anesthetic circuit.

When using the $O_2$ flush, however, if the flush is activated while the ventilator is in the inhalation cycle, that is, it is then in the process of forcing a breath into the patient, the exhalation valve is, of course closed, and the overall anesthesia system forms a closed system.

At that point, the $O_2$ flush provides a flow of oxygen, in an amount of up to about 75 liters/min., into a closed system and the natural consequence is a build up of pressure within the overall system and particularly in the patient circuit that is directly connected to the patient and in communication with the patient lungs.

The build up of pressure can reach pressures of 60–100 cm $H_2O$ and which can be an undesirable pressure to be reaching the patients lungs. Accordingly, a problem exists in the potential of harmful pressures reaching the lungs of a patient if the oxygen flush is activated during the time that the ventilator is in the inhalation cycle.

SUMMARY OF THE INVENTION

The anesthesia system of the present invention includes a means of preventing the possibility of a pressure build up in the patient circuit and, therefore, the lungs of a patient, without regard to whether the $O_2$ flush is activated by the user during the inhalation or the exhalation cycle of the ventilator.

In particular, the present system provides a means of detecting when the oxygen flush has been activated and opens a valve, preferably the exhalation valve, to vent the patient circuit when the oxygen flush has been activated. The invention may be carried out in a number of ways. For example, in the preferred embodiment, the activation of the oxygen flush valve may simply send an electronic signal to the CPU controlling the ventilator and query what cycle is currently being used. If the ventilator is in the inhalation cycle, the CPU would immediately change the cycle of the ventilator to the exhalation cycle. In accordance with the normal operation, the ventilator would then open the exhalation valve.

That signal could, on the other hand, be used to shorten the duration of the remaining inspiration cycle such that the gas volume delivered to the patient does not exceed the desired inspired volume. This approach requires, of course, an estimate of the flush and fresh gas flow, or combined flow rate in the inhalation limb, so that the total flow can be determined.

Alternatively, there can be a mechanical linkage between the activation of the flush valve and the exhalation valve such that the exhalation valve is physically opened by the mechanical means as the flush valve is activated.

As a further alterative, there may be an electrical or pneumatic signal provided to the exhalation valve directly from the flush valve to operate a solenoid or electrically operated exhalation valve or pneumatic actuated valve.

As still further alternatives, any of the foregoing controls can be used to open any vent valve interposed in communication with the patient circuit and which allows that patient circuit to vent, it being preferable, certainly, that such valve be in the exhalation side of the patient circuit so that the oxygen can carry out a complete flush of the patient circuit. As such, therefore, a separate vent valve may be added to the exhalation side of the patient circuit and activated separate of any other function of the anesthesia system and otherwise have no purpose in the system other than to provide protection against overpressuring the patient's lungs as described aforesaid.

Other objects, features and advantages of the present invention will be more apparent from the detailed description of the preferred embodiments set forth below, taken in conjunction with the accompanying drawings.

DESCRIPTION OF THE PREFERRED EMBODIMENT

Figure 1:
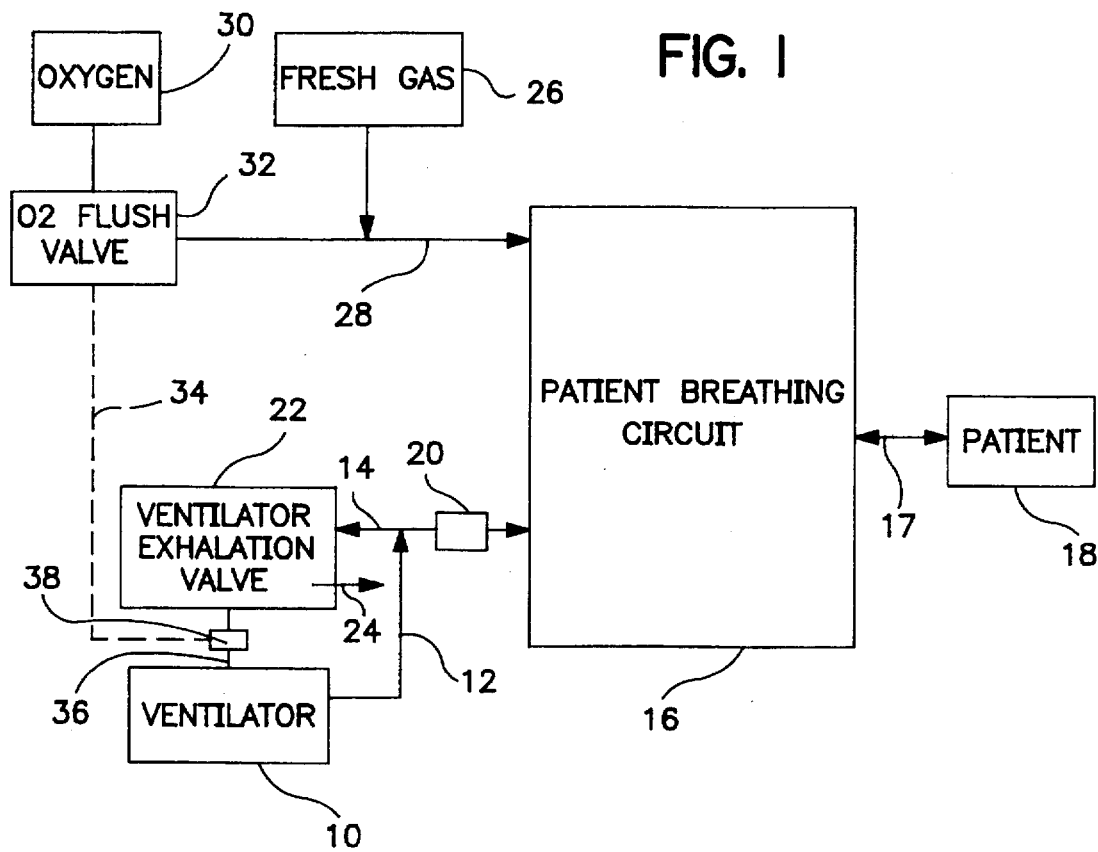
FIG. 1 is a block diagram of the components of one possible anesthesia system used to carry out the present invention.
Figure 2:
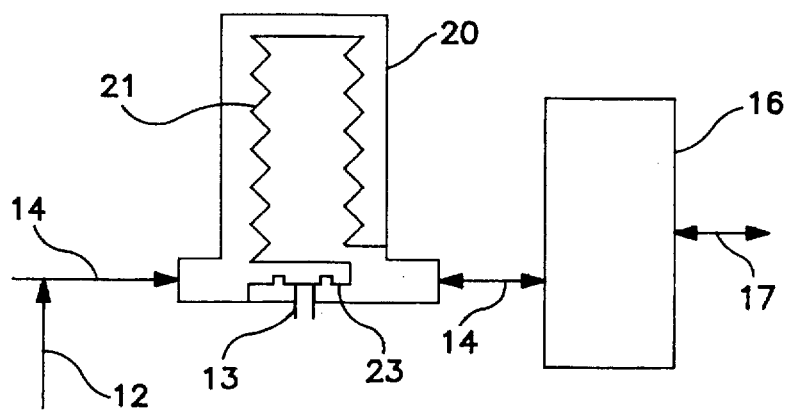
FIG. 2 is a schematic enlarger view of a bellows and bellows container used with the system of FIG. 1.

Referring now to FIGS. 1 and 2, there is shown a block diagram of an anesthesia system adapted to carry out the subject invention and an enlarged schematic view of the bellows canister and bellows usable with the present system. As shown, a ventilator 10 is provided and which may be of the type shown and described in U.S. Pat. No. 5,315,989 assigned to the present applicant and the disclosure of which is incorporated herein by reference. That ventilator 10 of the aforementioned U.S. Patent has an inhalation cycle and an exhalation cycle controlled by a CPU.

The ventilator 10 provides gas to the patient during the inhalation cycle via a conduit 12 and a conduit 14 to the patient breathing circuit 16 where it is delivered to the patient 18. As has been explained, a bellows assembly 20 may be included and which is powered by the ventilator 10. When a bellows assembly 20 is present in the anesthetic system, air or other powering gas is supplied to the bellows assembly 20, exterior of the bellows 21 and which then collapses the bellows 21 to force gases within the bellows 21 to the patient 18. Other gas conduits are not shown, however, the system using a bellows assembly 20 is conventional and the anesthetic laden gas is contained within the bellows 21 and a pneumatic circuit is used where some of the exhalation of the patient can be rebreathed by the patient.

As will become apparent, the oxygen flush system of the present invention can be used whether the system utilizes a bellows assembly or whether the breathing mixture is directly introduced into the patient from the ventilator 10.

As also noted in the aforementioned U.S. Patent, the breathing circuit 16 itself conventionally includes an inspiration limb and an expiration limb and the patient is connected to a wye connection shown schematically at 17 located intermediate the inspiration and the expiration limbs. The means of connection may be an endotracheal tube, face mask or other interface between the patient 18 and the patient breathing circuit 16. Alternatively, the patient circuit may be a common circuit known as a Bain circuit where coaxial conduits carry gas to and from the patient.

Accordingly, as is conventional, when the ventilator 10 is in its inhalation cycle, a supply of gas, containing a controlled concentration of an anesthetic, is forced through the patient breathing circuit 16 and into the patient 18.

A ventilator exhalation valve 22 is shown which may indirectly control the popoff valve 23 to relieve the gasses in the patient breathing circuit 16 and may be a component of the ventilator 10 or may be a separate component. The ventilator exhalation valve 22 is also connected to and in communication with the patient breathing circuit 16 by means of the conduit 14 and may be teed off of the same conduit that provides the breathing air to the patient breathing circuit 16.

During inspiration of the patient 18, the ventilator exhalation valve 22 and the popoff valve 23 are both in the closed position so that all of the gas forced from the ventilator 10 is used to inflate the patients lungs (directly or through the bellows assembly 20). During the exhalation cycle of the ventilator 10, as again is conventional, the ventilator 10 discontinues the flow of forced gas toward the patient 18 and the ventilator exhalation valve 22 opens so that the patient can exhale, either by means of the bellows assembly 20 where the pressure is relieved on the bellows and the patient can exhale into the bellows to inflate that bellows or directly exhale to the atmosphere or to a scavenging system where a bellows is not employed. If a bellows is employed, the opening of the ventilator exhalation valve 22 indirectly permits the popoff valve 23 to open when the bellows is fully inflated. This further relieves the enclosed patient exhaled gasses to a scavenging system by means of conduit 13. As shown, the ventilator exhalation valve 22 normally operates by opening the conduit 14 through a vent 24 to the atmosphere.

The ventilator exhalation valve 22 is therefore open during the exhalation cycle of the ventilator 10, and the pressure in the patient breathing circuit 16 (directly or indirectly) is reduced to ambient and the patient can freely exhale.

As further components to the typical anesthesia system, a fresh gas supply 26 is provided and which supplies fresh gas to the patient breathing circuit 16 to replace the gases that are taken up by the patient and/or vented from the system through various means. The fresh gas supply 26 is connected to the patient breathing circuit 16 via a conduit 28 and provides the fresh gas into the inspiratory limb of the patient breathing circuit 16.

An oxygen flush feature is provided to flush out the patient breathing circuit 16 as well as other conduits of the anesthesia system and, as shown, a supply of oxygen 30, under pressure, supplies an oxygen flush valve 32 which can be activated by the user to flush out the system as desired.

The $O_2$ flush valve 32 is conventionally a pushbutton valve that activates the oxygen flush when the user depresses the pushbutton of the $O_2$ flush valve 32 and deactivates the oxygen flush when the user releases the $O_2$ flush valve 30. Accordingly, the operation of the $O_2$ flush valve 30 is to cause a flow of oxygen into the system for a quick flushing thereof by the user manually pushing the $O_2$ flush valve 32 for whatever amount of time is deemed necessary.

As stated, if the user activates the oxygen flush, a flow of up to 75 liters per minute of oxygen enters conduit 28 and is directed to the inspiratory limb of the patient circuit 16 to continue therethrough to flush out the anesthesia system. In the event the user activates the oxygen flush during the period of time that the ventilator 10 is in the inhalation cycle, that is, the ventilator 10 is currently providing a breath to the patient 18, the ventilator exhalation valve 22 is closed and therefore the flow of oxygen is forced into a closed system, resulting in a build up of pressure in that system.

The build up of pressure includes the patient breathing circuit 16 and correspondingly therefore, the lungs of the patient 18 who is directly connected thereto. The build up of pressure can reach unacceptable levels in the lungs and therefore is an undesirable effect.

In accordance with the present invention, a signal line 34 provides a signal to the ventilator exhalation valve 22 whenever the $O_2$ flush valve is activated by the user and which causes the ventilator exhalation valve 22 to immediately open to vent the patient breathing system 16 and thereby prevent the build up of pressure. Thus, the ventilator exhalation valve 22 opens no matter which cycle is currently being delivered by the ventilator 10, that is, if the ventilator 10 is already in the exhalation cycle, the ventilator exhalation valve 22 is already open and the signal through signal line 34 is basically redundant.

If, however, the ventilator 10 is in the inhalation cycle when the $O_2$ flush valve 32 is activated, the signal provided through the signal line 34 will override the normal closure of the ventilator exhalation valve 22 and cause it to immediately open. Therefore, no matter what cycle the ventilator 10 is in at the time, the activation of the $O_2$ flush valve 32 by the user will allow the venting of the patient breathing circuit 16 to prevent the aforementioned undesirable build up of pressure that could affect the lungs of the patient 18.

Obviously, the type of ventilator exhalation valve 22 that is used in the anesthesia circuit will determine the particular signal used to open that valve. For example, if the ventilator exhalation valve 22 is a solenoid operated valve, the signal from the $O_2$ flush valve may be a simple electrical signal to open the ventilator exhalation valve 22. In the FIG. 1 preferred embodiment, a control line 36 is shown that controls the ventilator exhalation valve 22 from the ventilator 10 and a bleed valve 38 in interposed in that control line 36.

Again, the preferred embodiment is being described in where the ventilator exhalation valve 22 is used to vent the patient breathing circuit 16 inasmuch as that function valve is already present in most anesthesia circuits and therefore can conveniently be used to carry out the purpose of the present invention. In the alternate, however, as will become clear, a separate valve may be used in the system to specifically have the purpose of venting the patient breathing circuit 16 in carrying out the present invention.

Turning now to FIG. 2, there is shown a schematic view of the preferred embodiment of the present invention where the ventilator exhalation valve 22 is of the commercial design and which is shown and described in the aforementioned U.S. Pat. No. 5,315,989 of Tobia. As shown, the ventilator exhalation valve 22 thus receives the exhaled gases via the conduit 14 and, when the ventilator exhalation valve 20 is opened, vents those gases via the vent 24 to ambient atmosphere. A diaphragm 40 controls the opening and closing of the passageway between conduit 14 and the vent 24 and is responsive to the pressure in a diaphragm chamber 42 which receives a pneumatic signal from the ventilator via the control line 36.

Accordingly, as the $O_2$ flush valve 32 of the present invention is activated by the user, a signal may be provided through the signal line 34 in the form of an electrical signal activate bleed valve 38 to vent the line 36 via vent 42 to cause the pressure in diaphragm chamber 36 to be reduced to atmospheric pressure. Thus the ventilator exhalation valve 20 would immediately open to vent the patient circuit and prevent the overpressuring of the patient breathing circuit 16. (not shown in FIG. 2). In such case, the bleed valve 38 would be a solenoid operated valve and thereby be movable between its open and closed positions through an electrical control signal.

Alternatively, the bleed valve 38 may be a pneumatically operated valve and the signal from the $O_2$ flush valve along signal line 34 may be a pneumatic signal and activate pneumatically operated bleed valve 38 to open that valve and operate to vent the diaphragm chamber 42 in a similar fashion.

As a further alternative, there can easily be a physical, mechanical connection between the $O_2$ flush valve 32 and the bleed valve 38 such that when the $O_2$ flush valve 32 is pushed, a cable or rod could directly be connected to the bleed valve 38 to open the bleed valve 38 when the $O_2$ flush valve 32 is pushed by the user.

Figure 3:
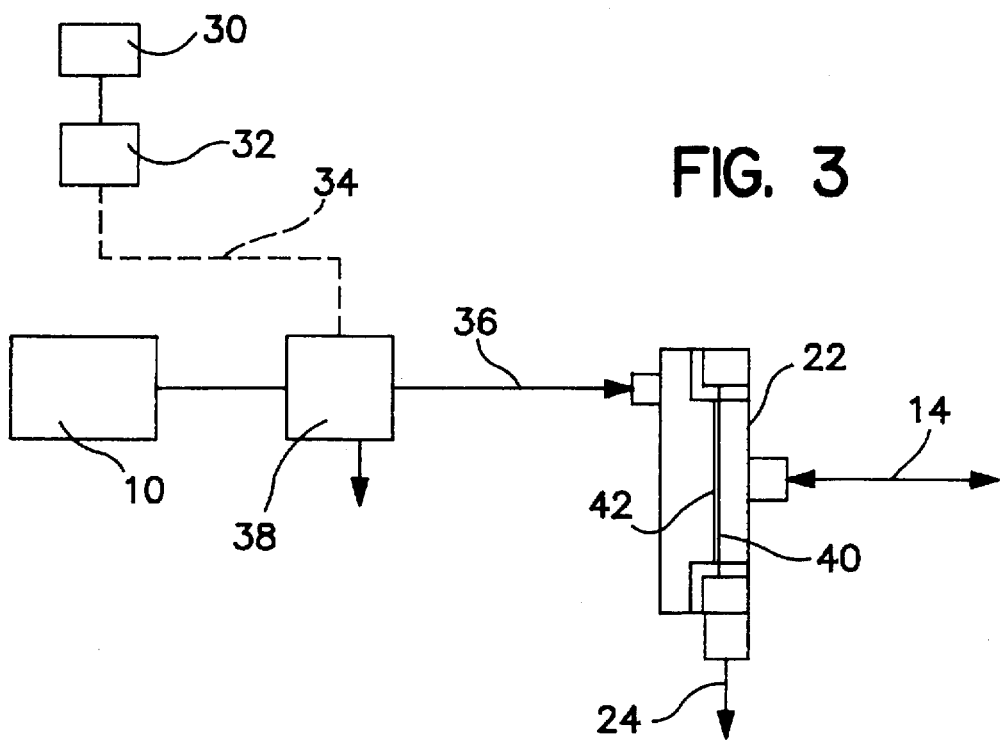
FIG. 3 is a schematic view of one embodiment of the control system used to carry out the present invention.
Figure 4:
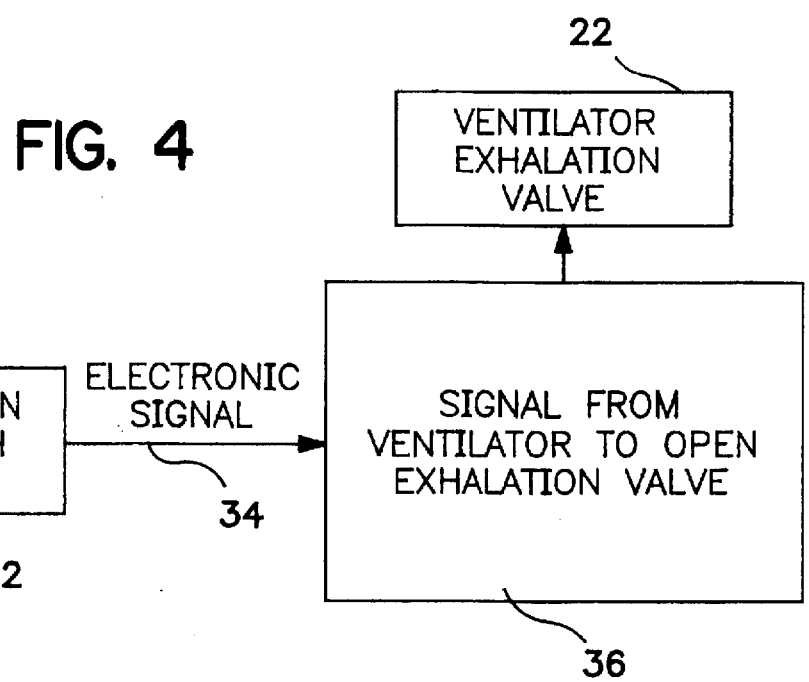
FIG. 4 is a block diagram of the preferred embodiment of the system used to carry out the present invention.

Turning, finally to FIG. 3, there is shown a block diagram of the preferred embodiment used in controlling the ventilator exhalation valve 22, this means operating through the ventilator 10 itself. In this embodiment, upon activation of the $O_2$ flush valve 32 by the user, an electronic signal is sent directly to the ventilator 10 to indicate that the $O_2$ flush valve 32 has been activated.

The ventilator 10 has a CPU, again as described in the U.S. Pat. No. 5,315,989 and the CPU can readily recognize the signal and immediately switch the ventilator to the exhalation cycle. That change in cycle causes the normal ventilator commands to open the ventilator exhalation valve 20 without any further signals or added components to the anesthesia system. As the $O_2$ valve is thereafter deactivated, the signal to the CPU is ceased and the CPU can return the ventilator 10 to its normal operation.

As a further improvement to immediately placing the ventilator into the exhalation cycle, the ventilator CPU can estimate a reduced amount of time remaining and shorten the inhalation cycle and allow the ventilator to deliver the appropriate breath volume to the patent before switching to the exhalation cycle. Obviously, to properly determine that reduced amount of time needed to provide the desired breath to the patient, the ventilator CPU must know, or have an accurate estimate, of the fresh gas flow so that flow can be taken into account when determining that time necessary to ventilate the patient as desired.

While the present invention has been set forth in terms of a specific embodiment, it will be understood that the anesthesia system herein disclosed may be modified or altered by the those skilled in the art to other configurations, Accordingly, the invention is to be broadly construed and limited only by the scope and spirit of the claims appended hereto.

We claim:

1. An anesthesia system for providing anesthesia to a patient, the combination comprising;
   a patient circuit adapted to be connected to a patient for delivering and receiving gas from a patient's lungs,
   a valve in communication with said patient circuit, said valve adapted to be opened to vent said patient circuit to an external environment,
   a ventilator for providing a quantity of gas to said patient circuit for delivery to the patient; said ventilator having an inhalation mode where the gas is supplied to a patient and an exhalation mode where the gas is received from a patients exhalation;
   a supply of oxygen under pressure,
   a conduit communicating said supply of oxygen with said patient circuit,
   a control means in said conduit operable by the user to activate the supply of oxygen to enter and flush the patient circuit,
   means responsive to the activation of said control means to flush said patient circuit to positively open said valve independent of the pressure in the patient circuit to vent said patient circuit and prevent the build up of pressure in said patient circuit.

2. An anesthesia system as defined in claim 1 wherein said means responsive to the activation of said control means is an pneumatic signal and said valve is a pneumatically operable valve.

3. An anesthesia system as defined in claim 1 wherein said means responsive to the activation of said control means is a mechanical linkage opening said valve.

4. An anesthesia system as defined in claim 1 wherein said means responsive to the activation of said control means is an electrical signal and said valve is an electrically operable valve.

5. In an anesthesia system for providing anesthesia to a patient, the combination comprising;
   a patient circuit adapted to be connected to a patient for delivering and receiving gas from a patient's lungs,
   a ventilator for providing a quantity of gas to said patient breathing circuit for delivery to a patient, said ventilator having an inhalation mode where the gas is supplied to a patient and an exhalation mode where the gas is received from a patients exhalation;
   an exhalation valve in communication with said patient circuit, said exhalation valve venting said patient circuit when said ventilator is in the exhalation mode,
   a supply of oxygen under pressure,
   a conduit communicating said supply of oxygen with said patient circuit,
   a control means in said conduit operable by a user to activate the supply of oxygen to enter and flush the patient circuit,
   means responsive to the activation of said control means to flush said patient circuit to positively open said valve independent of pressure within said patient circuit to vent said patient circuit and prevent the build up of pressure in said patient circuit.

6. In an anesthesia system as defined in claim 5, the improvement wherein said means responsive to the actuation of said control means provides an electronic signal to said ventilator to switch said ventilator to the exhalation mode.

7. In an anesthesia system as defined in claim 6, the improvement wherein said electronic signal returns said ventilator to the inhalation mode when said control means is deactivated.

8. In an anesthesia system as defined in claim 5, the improvement wherein said means responsive to the actuation of said control means provides an electronic signal to said ventilator to decrease the inhalation time cycle and to terminate said inhalation cycle when a predetermined amount of gas has been administered to the patient.

9. In an anesthesia system as defined in claim 5, the improvement wherein said means responsive to the actuation of said control means provides an pneumatic signal to activate said valve.

10. In an anesthesia system as defined in claim 5, the improvement wherein said exhalation valve comprises a diaphragm and a chamber that is pressurized to act against said diaphragm to close said valve, and said means responsive to said actuation of said control means opens said valve by reducing the pressure within said chamber.

11. In an anesthesia system as defined in claim 10, the improvement wherein said means responsive to said actuation of said control means reduces the pressure within said chamber by venting said chamber.

12. In an anesthesia system as defined in claim 11, the improvement wherein said control means comprises a valve actuated by a pushbutton that activates said valve when pushed and deactivates said valve when released.

13. A method of preventing the build up of excessive pressure within a patient circuit comprising the steps of;
   providing a ventilator for supplying a breath to a patient during the inhalation mode and for allowing the patient to exhale during the exhalation mode;
   providing a valve in communication with the patient circuit that is openable to vent the patient circuit;
   providing a supply of oxygen under pressure to the patient circuit;
   activating the supply of oxygen to the patient circuit to flush the patient circuit as directed by a user; and
   positively opening the valve to vent the patient circuit independent of the pressure within the patient circuit when the user activates the supply of oxygen to flush the patient circuit.

14. A method as defined in claim 13 wherein said step of opening said valve comprises providing an electrically operated valve and further providing an electrical signal to the valve when said supply of oxygen is activated.

15. A method as defined in claim 13 wherein said step of providing a ventilator comprises providing a ventilator having an inspiratory and an expiratory cycle controlled by a processor and said step of opening said valve includes providing an electrical signal to the processor to change the cycle to the exhalation cycle.

16. A method as defined in claim 13 wherein said step of providing a ventilator comprises providing a ventilator having a timed inspiratory and a timed expiratory cycle controlled by a processor and said step of opening said valve includes providing an electrical signal to the processor to reduce the inspiratory phase time a predetermined amount and opening said valve after said shortened inspiratory phase has provided a predetermined amount of gas to the patient.

\* \* \* \* \*